(12) United States Patent
Derhy et al.

(10) Patent No.: US 11,668,571 B2
(45) Date of Patent: *Jun. 6, 2023

(54) SIMULTANEOUS LOCALIZATION AND MAPPING (SLAM) USING DUAL EVENT CAMERAS

(71) Applicant: SAMSUNG ELECTRONICS CO., LTD., Suwon-si (KR)

(72) Inventors: Sebastien Derhy, Tel Aviv (IL); Lior Zamir, Ramat Hasharon (IL); Nathan Henri Levy, Givatayim (IL)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 255 days.

This patent is subject to a terminal disclaimer.

(21) Appl. No.: 17/176,500

(22) Filed: Feb. 16, 2021

(65) Prior Publication Data
US 2021/0190497 A1 Jun. 24, 2021

Related U.S. Application Data

(63) Continuation of application No. 16/030,273, filed on Jul. 9, 2018, now Pat. No. 10,948,297.

(51) Int. Cl.
*G01C 21/20* (2006.01)
*G06T 7/579* (2017.01)
(Continued)

(52) U.S. Cl.
CPC ...... *G01C 21/206* (2013.01); *A61B 1/000094* (2022.02); *G01C 21/3848* (2020.08);
(Continued)

(58) Field of Classification Search
CPC .......... G01C 21/16; G01C 21/32; G06T 7/579
See application file for complete search history.

(56) References Cited

U.S. PATENT DOCUMENTS

2005/0182518 A1   8/2005   Karlsson
2008/0144925 A1   6/2008   Zhu et al.
(Continued)

FOREIGN PATENT DOCUMENTS

| CN | 107506722 | 12/2017 |
| CN | 109029417 | 12/2018 |
| WO | 2018037079 | 3/2018 |

OTHER PUBLICATIONS

Bylow, E., et al., "Real-Time Camera Tracking and 3D Reconstruction Using Signed Distance Functions", Robotics: Science and Systems, 2, (2013), (8 pages).
(Continued)

*Primary Examiner* — Frederick M Brushaber
*Assistant Examiner* — Elizabeth Yang
(74) *Attorney, Agent, or Firm* — F. Chau & Associates, LLC

(57) ABSTRACT

A method for simultaneous localization and mapping (SLAM) employs dual event-based cameras. Event streams from the cameras are processed by an image processing system to stereoscopically detect surface points in an environment, dynamically compute pose of a camera as it moves, and concurrently update a map of the environment. A gradient descent based optimization may be utilized to update the pose for each event or for each small batch of events.

20 Claims, 14 Drawing Sheets

(51) Int. Cl.
- *G01C 21/00* (2006.01)
- *G06T 7/73* (2017.01)
- *A61B 1/00* (2006.01)
- *G06V 10/75* (2022.01)
- *G06V 10/44* (2022.01)
- *G06V 20/56* (2022.01)
- *G01C 21/16* (2006.01)

(52) U.S. Cl.
CPC ............... *G06T 7/579* (2017.01); *G06T 7/73* (2017.01); *G06V 10/44* (2022.01); *G06V 10/757* (2022.01); *G06V 20/56* (2022.01); *G01C 21/16* (2013.01)

(56) References Cited

U.S. PATENT DOCUMENTS

| | | | | |
|---|---|---|---|---|
| 2014/0125700 | A1* | 5/2014 | Ramachandran | G09G 5/377 345/633 |
| 2014/0139639 | A1* | 5/2014 | Wagner | H04N 13/204 348/46 |
| 2016/0147230 | A1 | 5/2016 | Munich et al. | |
| 2017/0230633 | A1 | 8/2017 | Doh | |
| 2019/0035098 | A1 | 1/2019 | Pinard | |
| 2019/0035100 | A1* | 1/2019 | Ebrahimi Afrouzi | G06V 20/10 |
| 2019/0197715 | A1 | 6/2019 | Rebecq et al. | |
| 2019/0226852 | A1 | 7/2019 | Xie et al. | |
| 2019/0340435 | A1 | 11/2019 | Rabinovich et al. | |
| 2020/0011668 | A1 | 1/2020 | Derhy et al. | |

OTHER PUBLICATIONS

Curless, B., et al. "A volumetric method for building complex models from range images", Proceedings of the 23rd annual conference on Computer graphics and interactive techniques, (1996) (10 pages).

Henri Rebecq, et al., "EVO: A Geometric Approach to Event-based 6-DOF Parallel Tracking and Mapping in Real-time", IEEE Robotics and Automation Letters, (2016), (8 pages).

Kim, H., et al., "Real-time 3D reconstruction and 6-DoF tracking with an event camera", European Conference on Computer Vision, (2016). (16 pages).

Klein, G., et al., "Parallel Tracking and Mapping far Small AR Workspaces", ISMAR(1997) (10 pages).

Newcombe, R. A., et al., "KinectFusion: Real-time dense surface mapping and tracking", 2011: IEEE (10 pages).

Weikersdorfer, D., et al., "Event-based 3D SLAM with a depth-augmented dynamic vision sensor. Robotics and Automation", (ICRA), 2014 IEEE International Conference on, (2014).(pp. 359-364).

CN107506722A Facial emotion recognition method based on deep sparse convolutional neural network, 2017, Weihua (Year: 2017); related U.S. Appl. No. 16/030,273, 13 pages.

* cited by examiner

SIMULTANEOUS LOCALIZATION AND MAPPING (SLAM) USING DUAL EVENT CAMERAS

CROSS REFERENCE TO RELATED APPLICATION

This application is a continuation under 35 U.S.C. 120 of U.S. patent application Ser. No. 16/030,273, filed in the U.S. Patent and Trademark Office on Jul. 9, 2018, the contents of which are incorporated by reference herein in its entirety.

TECHNICAL FIELD

The present disclosure relates generally to computer vision and simultaneous localization and mapping (SLAM).

DISCUSSION OF THE RELATED ART

SLAM is a technique for simultaneously mapping a sensed environment and calculating the position of a device relative to the mapped environment. The device may be a camera-equipped movable device such as a robot, a drone, a hand-held smart phone, an autonomous vehicle, etc. that may have no advanced knowledge of the environment. A subset of SLAM called Parallel Tracking and Mapping (PTAM) employs parallel processing threads for tracking a device's position and mapping. One thread maps the environment by detecting and maintaining a set of salient visual landmarks visible through the camera. Another thread, i.e., a pose tracking thread, frequently updates the camera position relative to the visible landmarks.

SUMMARY

In accordance with the inventive concept, a SLAM method employs dual event cameras. The cameras are used in conjunction with an image processing system to stereoscopically detect surface points in an environment, dynamically compute pose of a camera as it moves, and concurrently update a map of the environment.

In an illustrative embodiment, a SLAM method involves receiving, from first and second image sensors, a first event stream and a second event stream, respectively, of asynchronous events representing surface points in an environment. The first and second image sensors are arranged with overlapping fields of view to enable epipolar depth measurements of the points. A pose of at least the first image sensor with respect to a reference element in the environment is dynamically computed as the camera moves; and concurrently, a map of the environment is dynamically updated, based at least on the points represented by the first event stream and the computed depths thereof.

A gradient descent based optimization may be utilized to update the pose for each event or for each small batch of events.

In an embodiment, a SLAM system may include a first image sensor that provides a first event stream of asynchronous events representing points of surfaces in an environment; a second image sensor arranged to have an overlapping field of view with that of the first image sensor and providing a second event stream of asynchronous events representing points of surfaces in the environment; and an image processing system comprising at least one processor. The at least one processor may execute instructions read from a memory to: compute depths from the first and second image sensors stereoscopically based on common points of matching features represented by the first and second event streams; and dynamically compute a pose of at least the first image sensor with respect to a reference element in the environment, and update a map of the environment, based at least on the matching feature points represented by the first event stream and the computed depths thereof.

Various embodiments may exhibit advantages over conventional SLAM systems such as reduced power consumption, reduced latency, reduced jitter, and robustness to high speed motion.

BRIEF DESCRIPTION OF THE DRAWINGS

The above and other aspects and features of the inventive concept will become more apparent from the following detailed description, taken in conjunction with the accompanying drawings in which like reference numerals indicate like elements or features, wherein.

DETAILED DESCRIPTION OF EMBODIMENTS

Figure 1:
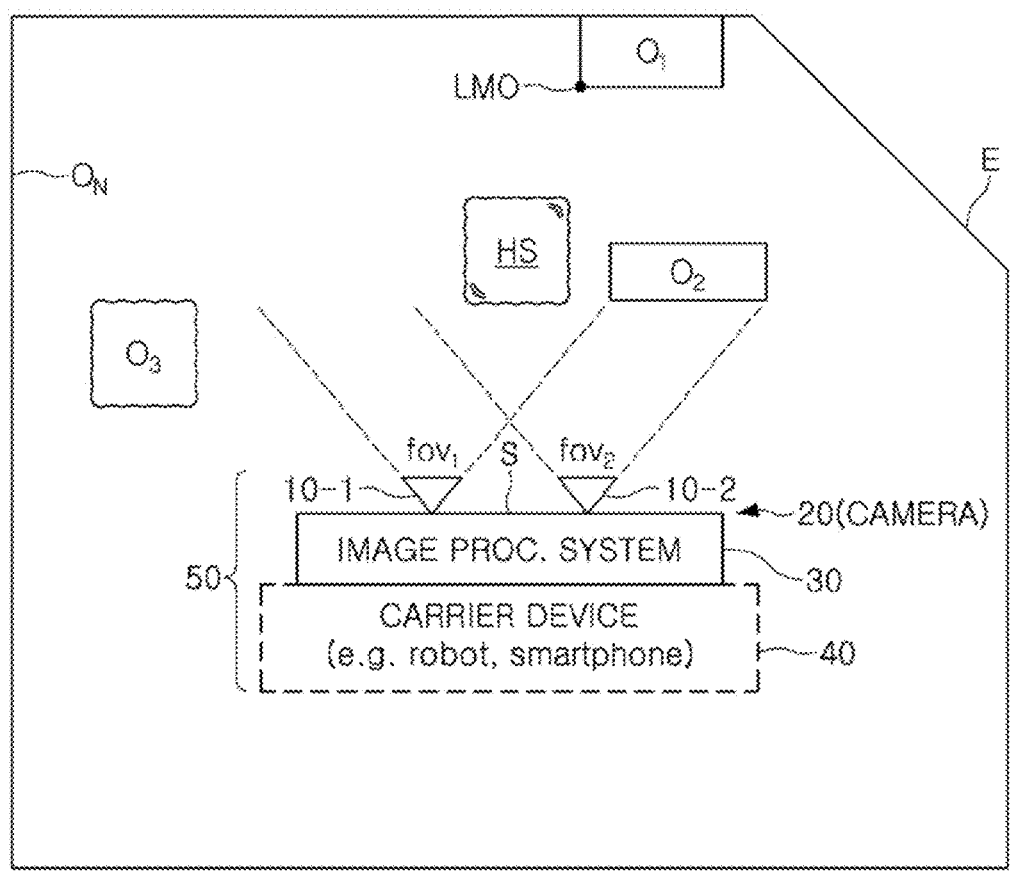
FIG. 1 schematically illustrates an environment in which a camera-equipped device may perform SLAM in accordance with the inventive concept.

The following description, with reference to the accompanying drawings, is provided to assist in a comprehensive understanding of certain exemplary embodiments of the inventive concept disclosed herein for illustrative purposes. The description includes various specific details to assist a person of ordinary skill the art with understanding the inventive concept, but these details are to be regarded as merely illustrative. For the purposes of simplicity and clarity, descriptions of well-known functions and constructions may be omitted when their inclusion may obscure appreciation of the inventive concept by a person or ordinary skill in the art.

The inventive concept employs a stereoscopic event-based camera in conjunction with optimization-based image processing to achieve simultaneous localization and mapping that affords certain advantages over known systems. For instance, conventional SLAM methods typically take a monocular approach in which a single camera captures a scene image. Monocular systems have no measurement of scale of the environment and therefore rely on an external source for this information. Typically, this is done by measuring depth of image points using a laser, time of flight, sonar or other method. Further, even if this environmental scale information is provided during system initialization, unless it is continuously provided, the scale information will tend to drift once the camera explores new areas away from the initial position. The scale may always be inferred indirectly based on the initial scale measurement. Hence monocular systems often exhibit problems of scale ambiguity and scale drift.

Other drawbacks with monocular systems are delayed feature initialization and special system initialization requirements. In a monocular SLAM system depth information for new image features may be derived only once the camera center has moved sufficiently from a previous location. During this time the system maintains accurate tracking using existing features (which are typically not within the entire field of view when new features are visible) and hence the system is prone to failure when exploring new areas. To initially identify features for tracking, a special initialization phase may be defined, with user cooperation often required.

In accordance with the inventive concept, when working with a calibrated stereo system with two image sensors, the scale information may be extracted by performing stereo matching between the two sensors. Further, the use of event cameras facilitates the stereo matching process because only information from a very short time interval may be considered for matching, and indeed may be the only information relevant. The stereo system may be used to insert new features into a maintained feature map in a mapping thread of PTAM. It may do so by first detecting prominent features in an image captured by one of the cameras and for each feature perform a constrained epipolar search in the second camera. A feature that has a match in the second camera can be triangulated to obtain an estimate of its depth and then inserted into the map.

In general, visual odometry (VO) is a process of determining the position and orientation of a moving device such as a robot by analyzing associated camera images. When multiple image sensors are used for VO, the orientation and position of these sensors, if unknown, may be determined from the sensors' measurements. The inventive concept may use VO—which usually requires some map awareness—as part of a SLAM system. A SLAM system may simultaneously estimate a camera's 6-Degrees of Freedom pose (6-DoF, namely 3 DoF for position, and 3 DoF for orientation) and a 3D map of its surroundings. The pose and 3D map are useful information components in many systems (e.g. virtual reality (VR), augmented reality, automotive navigation, drone navigation, domestic robots, etc.). If a particular application only requires pose tracking (e.g. VR) or just mapping (e.g. 3D scanning), it is desirable to estimate the other component as well, since this may result in a higher level of robustness.

FIG. 1 schematically depicts an environment in which a camera-equipped device may perform SLAM in accordance with the inventive concept. A camera equipped device 50 includes a carrier 40 such as a robot, a smartphone, a vehicle, a drone, etc., and a mounted camera 20. Device 50 may determine its initial position in a constrained or unconstrained environment E, generate an initial map of the environment, and track its position while building up the map as it moves within the environment. In the example of FIG. 1, a top view of a wall-confined environment is illustrated for simplicity of explanation, where the environment may include a horizontal ground surface HS detectable through image capture/pattern recognition by device 50. A volumetric map may be generated with objects in the environment such as O1, O2, O3 . . . ON of various characteristics, e.g., feature-rich objects, boundary objects, etc. situated in random locations.

Camera 20 may be a stereoscopic type camera with a first image sensor 10-1 and a second image sensor 10-2 (e.g., left and right image sensors) forming an image sensor pair. Image sensors 10-1, 10-2 are each "event sensors" such as dynamic vision sensors (DVSs), which asynchronously output image data with time stamps and pixel locations coinciding with "events" (described in detail later). The outputting of such events generates a relatively sparse data stream as compared to traditional video cameras which may output data for each pixel in every frame at a constant frame rate.

Hereafter, image sensors 10-1, 10-2 may each interchangeably be called an "event camera". Thus, camera 20 may be referred to herein as a "dual event camera". Camera 20 further includes an image processing system 30 that processes the asynchronous image data from image sensors 10-1, 10-2 to generate "event-frames", and performs SLAM processing. First and second images sensors 10-1, 10-2 have first and second fields of views fov1, fov2 that overlap one another, which allows image processing system 30 to compute a depth value for each commonly imaged point. Hence, camera 20 may also be referred to as a depth camera.

Figure 2A:
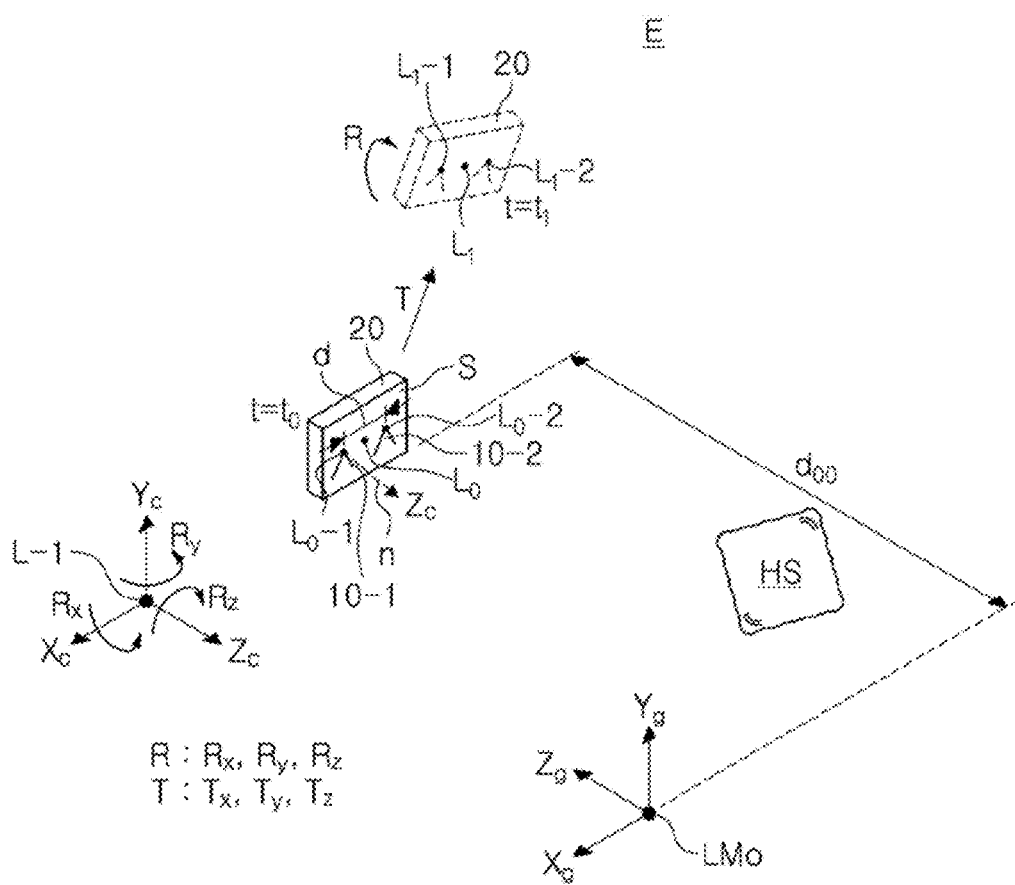
FIG. 2A illustrates a dual event-based camera in relation to a reference landmark in the environment of FIG. 1.

FIG. 2A illustrates camera 20 in relation to a reference landmark point LK) within environment E. Referring collectively to FIGS. 1 and 2A, first and second images sensors 10-1, 10-2 are calibrated to each other by having a known separation distance d across a surface S of camera 20, and by having a known relative orientation to each other. These parameters may be pre-stored and used by imaging processing system 30 to measure depths of object features and thereby create depth images. For instance, image sensors 10-1, 10-2 may have optical axes that are either parallel to each other or slightly tilted towards or away from one another by a predetermined angle. By knowing the separation distance d and relative orientation of the image sensors, image processing system 30 may calculate a distance from camera 20 to an object point in environment E that is commonly sensed by image sensors 10-1, 10-2. That is, z-direction depth of an imaged point may be computed based on the difference in relative positions within a first 2D event frame (in x-y space) captured by first image sensor 10-1 and a second event frame captured by second image sensor 10-2. (Hereafter, the first and second event frames may be referred interchangeably as first and second image frames, or as left and right images.)

A pose of a camera may be generally defined as the camera's location and orientation, with respect to a determined reference point (for location) and to a reference axial system (for orientation). In image processing/SLAM calculations described hereafter, individual poses of image sensors 10-1 and 10-2 may each be estimated through visual odometry. The pose of camera 20 is its location L and rotation R; image sensor 10-1 has a pose defined by its own location L-1 and rotation R-1; and image sensor 10-2 similarly has a pose defined by its location L-2 and rotation R-2. (For ease of explanation in the discussion below, the image sensors may be assumed to have parallel optical axes and their rotations may be assumed equal to a common rotation R of camera 20.) A local camera coordinate system with axes xc, yc, zc may be defined, where vector-based distances to points in the environment are estimated and measured with respect to the origin. In the example of FIG. 2A, the origin is at location L-1. A normal n extending perpendicularly from surface S may be assumed aligned with axis zc and assumed parallel to the optical axes of image sensors 10-1, 10-2. Axes xc and yc may be arbitrarily defined. The local coordinate system may be transformable to a global coordinate system of environment E with axes xg, yg, zg.

In an initialization process for tracking and mapping, an initial location $L_0$ of camera 20 (or initial locations $L_0$-1, $L_0$-2 of image sensors 10-1, 10-2) may be determined relative to at least one reference landmark point $LM_0$ detected in environment E. This occurs at an initial time $t_0$ at which a global reference frame is generated through initial detection of events (discussed later). For instance, as shown in FIG. 1, reference landmark $LM_0$ may be a point on a feature, such as an edge feature or corner feature of object O1, captured by both image sensors 10-1 and 10-2. Landmark $LM_0$ may be determined from the left and right images as a point located at a depth $d_{00}$ in the zc direction from the initial location $L_0$ of camera 20. The global coordinate system with axes xg, yg, zg may be defined with an origin at landmark point $LM_0$ to establish a reference point and reference directions for mapping. For instance, each of axes xg and zg may be parallel to horizontal surface HS, while axis yg is perpendicular to surface HS. Positions of other features/objects may each be referenced to landmark point $LM_0$. Likewise, the initial location $L_0$ of camera 20, which may be referenced to landmark point $LM_0$, may itself be considered an origin in the camera tracking process, where subsequent pose positions may be referenced to location $L_0$ by a translation T.

It is noted here that in some embodiments, the initial pose may be estimated with the aid of an Inertial Measurement Unit (IMU) (not shown) included within carrier 40. The IMU includes an accelerometer and a gyroscope and may improve an initial guess of the pose (initially and/or when updating the pose).

The rotation R of camera 20 may be defined as having three components Rx, Ry and Rz (three degrees of freedom). In an example, the image processing system of camera 20 may identify the horizontal surface HS in the environment, so that the camera 20 rotation R may be defined relative to surface HS and the global axes at reference landmark point $LM_0$. An initial orientation of camera 20 may be defined as having a rotation $R_0$ based on the left and right images, which may be designated zero rotation, i.e., 0, 0, 0 (Rx=0, Ry=0, Rz=0).

In conjunction with determining the initial location $L_0$ and initial rotation $R_0$ in the initialization process, an initial mapping of the environment may be generated. To this end, an initial volumetric map in which surface points of the various objects relative to the reference point(s) $LM_0$ and reference surface HS (and/or other reference surfaces) may be determined and stored.

At a time t1 after the capture of the initial left and right images coinciding with the initial location $L_0$ and rotation $R_0$, the camera 20 may move by translation T to an updated location $L_1$. The translation T may be defined as a vector with three components Tx, Ty and Tz (three degrees of freedom). At the new location $L_1$ the camera may have rotated by an amount R. Thus, at time t1 camera 20 has an updated pose with rotation R (relative to $R_0$) and location changed by translation T (where T is the vector distance between locations $L_0$ and $L_1$). In accordance with the inventive concept, an estimation of the updated pose is identified based on changes in the captured images by the first and second sensors 10-1 and 10-2 stemming from newly detected events. In addition, new map points of objects in environment E may be obtained at the updated pose, and the initial map is updated. The SLAM methods discussed below describe ways to compute changes in pose and to build up the map based on changes in images due to detection of events.

FIGS. 2B-2E generally illustrate concepts of a method of updating a pose and a map in accordance with the inventive concept. The example illustrates how an initial pose and an initial map may be updated, but is also applicable to the updating of any current pose and current map. Briefly, the updating of a pose and map in the SLAM system may entail solving an optimization problem in which coordinates of points of a first 3D point cloud representing an environment E from a current viewpoint are compared to coordinates of corresponding points of a second 3D point cloud of the environment from a second viewpoint. Due to noise and other factors, image capture of light is imperfect and therefore not all points representing a common object point in the two point clouds will match. An optimization routine may then be run to best align the two point clouds and arrive at an optimum pose estimate and mapping estimate for each change in the camera 20 position.

Figure 2B:
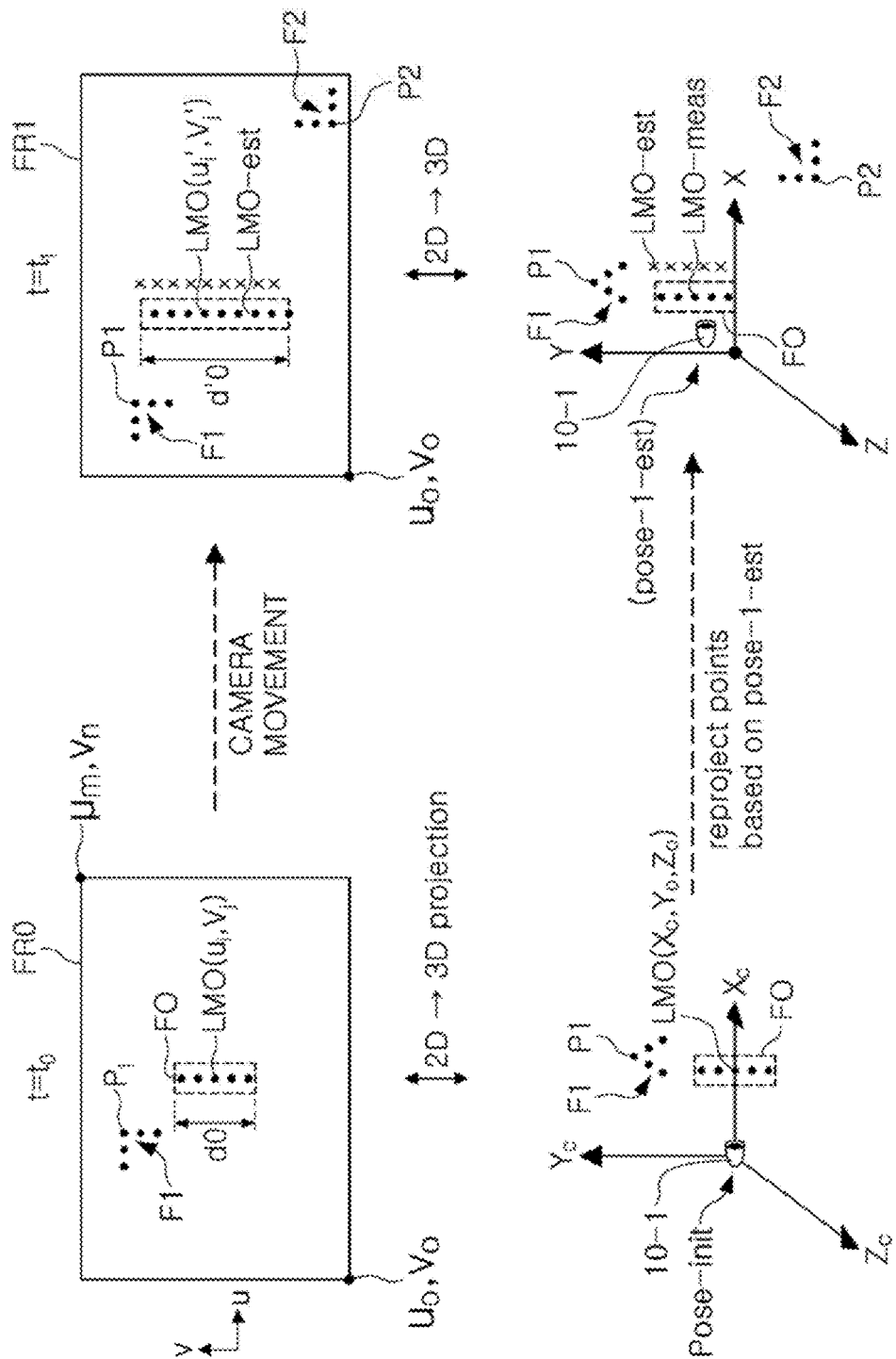
FIG. 2B illustrates concepts of a method of updating an initial pose and an initial map in accordance with the inventive concept.

In FIG. 2B, a first "event frame" FR0 may be designated a global reference frame representing a captured view of the environment E by camera 20 at an initial pose "pose-init" at time $t_0$. More specifically, event frame FR0 may be a 2D frame captured by image sensor 10-1 and is a frame defined by an (m×n) pixel grid with pixel coordinates u, v ranging from $u_0$, $v_0$ to $u_m$, $v_n$. Meanwhile, image sensor 10-2 also captures an event frame (not shown) which includes features F0 and F1 at pixel locations slightly offset from those in frame FR0. Since events from an event camera typically coincide with changes in brightness at the edges of objects, an event frame usually contains only sparse data. For simplicity, only two features F0 and F1 are shown in FIG. 2B, but an event frame may contain several, tens, hundreds or even thousands of features. Global reference frame FR0 may be referred to as a first keyframe, and subsequent frames may be referenced to frame FR0. Any subsequent frame may also be designated a keyframe, e.g., based on at least one predetermined criterion, such as whether more than a threshold number of new features are detected. Any given frame—whether a keyframe or a non-keyframe—may be registered to a keyframe.

Frame FR0 may have a feature F0, such as an edge of an object, which appears in frame FR0 with a length $d_0$. Feature F0 may be designated a landmark (LM) to which other features are compared. For simplicity of explanation, feature F0 is assumed to be identified with a landmark point $LM_0$ located at pixel coordinate $u_i$, $v_j$. Another feature F1 is a corner type feature shown having a corner point p1. Since features F0 and F1 are also imaged by second image sensor 10-2, their depths from camera 20 are calculated. Based on these depths, the fields of view of image sensors 10-1, 10-2, and the locations of the u, v pixel coordinates of the features, the 3D positions of features F0 and F1 may be computed in local camera coordinates xc, yc, zc. Thus, as part of an initial map, points representing surfaces of features F0 and F1 may be obtained and stored (where 3D coordinates in the camera coordinate system may be transformed to the global coordinate system of which landmark point $LM_0$ is used as a global reference origin).

Thereafter, at time t1, image sensor 10-1 captures event frame FR1 which includes the same features F0 and F1 but which appear at different pixel coordinates and geometries, since the features are imaged from a different viewpoint. In the example, features F0 and F1 have shifted leftward and appear larger than they did in frame FR0 (the length $d_0'$ of feature F1 is longer than length $d_0$ and the central pixel location has moved to ui', vj'). This signifies that camera 20 has moved rightward and closer to the features F0 and F1. Based on the change in pixel locations of features F0 and F1, and with knowledge of their previous locations in 3D space, image processing system 30 may compute an updated pose estimate "pose-1-est" for image sensor 10-1. This estimate may be refined through an iterative algorithm using an objective function, to obtain an optimized pose estimate.

In the pose estimate optimization process, as shown in FIG. 2B, an initial guess for a new pose estimate at time t1, "pose-1-est" may be made. In one embodiment, the initial guess may equal the previous pose. In other embodiments, the initial guess may differ from the previous pose based on a motion model or other approach. In the example of FIG. 2B, sensor 10-1 is assumed to have moved to a location used for an initial guess. (A close initial guess may result in a subsequent optimization algorithm converging relatively faster.) Feature points of the previous frame FR0 may then be re-projected to points corresponding to the pose guess for the current frame FR1. That is, as seen from the viewpoint of the pose guess, if the pose guess differs from that of the previous pose, estimated positions of the feature points (denoted with x's) will be shifted in the current frame FR1 relative to the previous frame FR0. At the pose guess, estimated coordinates such as LM0-est are thereby established for frame FR1.

Distances between these estimated coordinates and corresponding measured coordinates may be determined. The distances may then be inserted into an iterative optimization equation, such as a gradient descent based cost function, to refine the estimated pose. For instance, a measured coordinate LM0-meas is determined via a 2D-3D projection from its position in frame FR1, using the depth measurement based on two sensors 10-1, 10-2. The distance between the 3D coordinate LM0-est and the measured coordinate LM0-meas is obtained and used in the optimization equation. When an optimization routine based on the equation converges below a threshold, an optimized pose estimate is thereby obtained for the pose at time t1. The process is repeated with each new event frame to track the device 50's movement.

The same process as described above may be performed using event frames from the second image sensor 10-2 as a baseline. In this case, still more accurate poses may be computed.

It is also seen in FIG. 2B that event frame FR1 includes an additional feature F2 (comprised of points p2) that does not appear in frame FR0. Using the depth information, a 2D-3D projection may be made for the feature F2, and the 3D coordinates may then be stored in the map database, whereupon the map continues to be built. Since frame FR1 contains additional information, frame FR1 may itself be designated a keyframe that other frames may reference for updating of the pose and map with camera 20 movement.

Figure 2C:
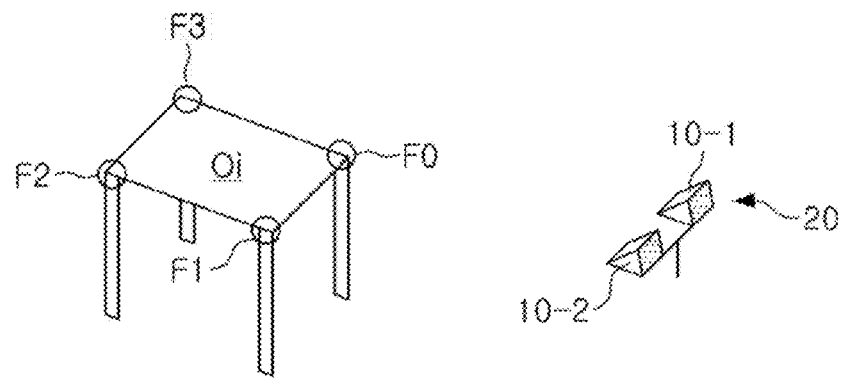
FIG. 2C illustrates identification of corner features of an object with first and second event cameras.
Figure 2D:
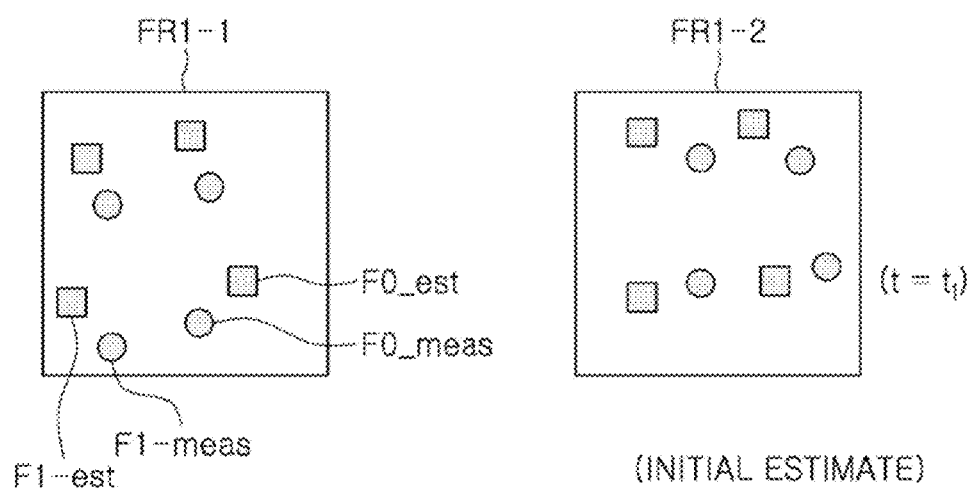
FIG. 2D shows a comparison of frame positions of measured feature points relative to estimated frame positions prior to an optimization process.
Figure 2E:
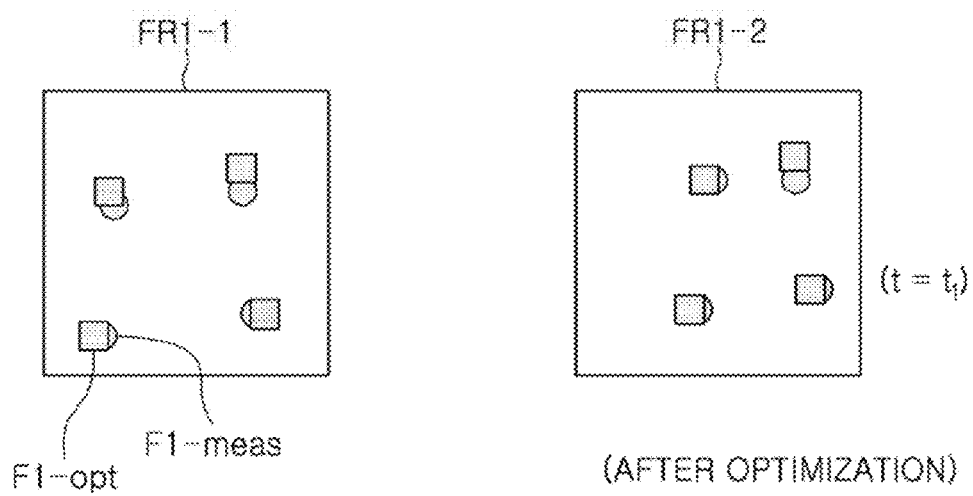
FIG. 2E shows the frame position comparison of FIG. 2D after an optimization process.

FIGS. 2C-2E illustrate an example of the above-mentioned pose optimization. FIG. 2C shows an object Oi having four corner features F0, F1, F2 and F3. The features are detected by each of image sensors 10-1 and 10-2 of event camera 20 at a time t1 following movement of event camera 20 from a previous position at which the features were also detected. FIG. 2D depicts two dimensional "event frames" (discussed below) FR1-1, FR1-2 generated from events captured by image sensors 10-1, 10-2, respectively at time t1. The circles shown in the event frames represent imaged (i.e., "measured") features such as F0-meas, F1-meas. The squares represent initial guesses of the positions of these features based on an initial guess of the new pose estimate discussed above. Distances between estimated features such as F0-est, F1-est and the corresponding measured features F0-meas, F1-meas, referred to as reprojection error, are determined and inserted into an optimization routine. The optimization routine, which optimizes an objective function for an optimized rotation and translation of camera 20, thereby computes a refined pose estimate at which the estimated feature positions are more closely aligned with the measured feature positions, as illustrated in FIG. 2E (the initially estimated position F1-est improves to "F1-opt" at the optimized pose). With regard to map building, using the optimized pose estimate, any new features detected at time t1 (although not shown in FIGS. 2D and 2E) may then be closely registered to landmark positions measured in previous frames. In addition, a bundle adjustment routine may be run to refine edges and other image elements of objects and thereby further refine the map.

Figure 3A:
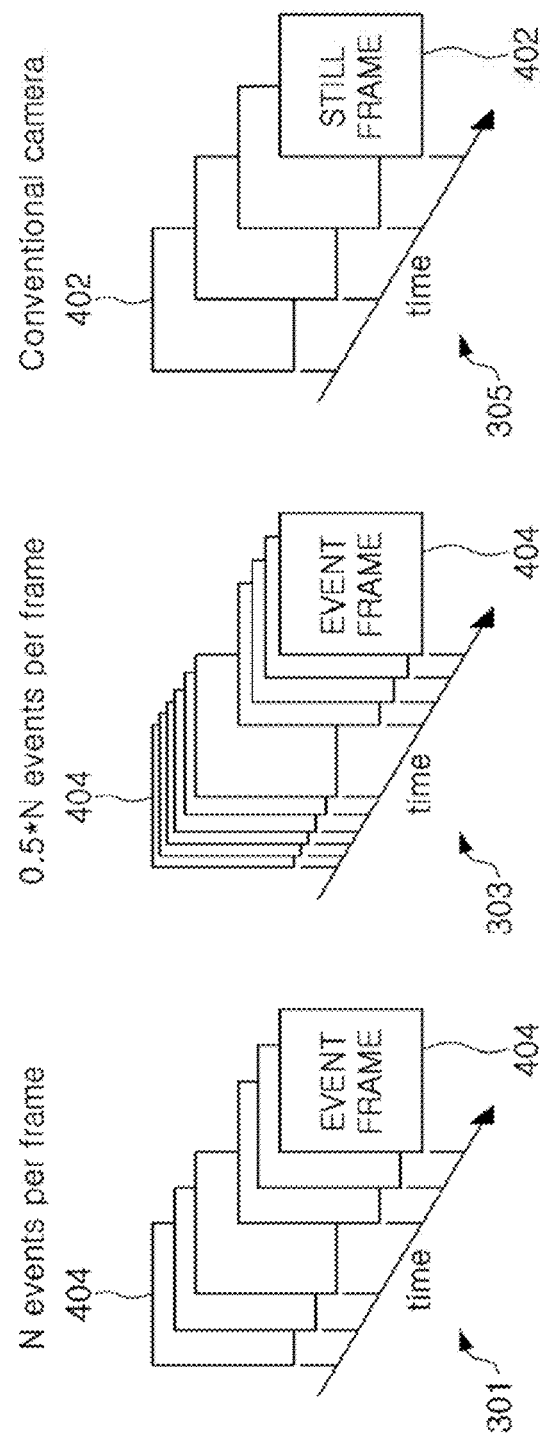
FIG. 3A illustrates event frame creation using an event camera, in comparison to frames created with a conventional video camera.
Figure 3B:
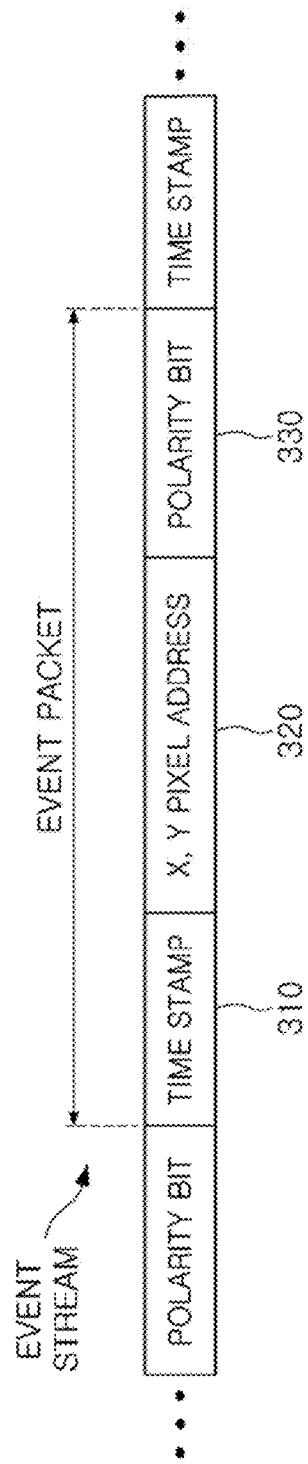
FIG. 3B shows an example structure of an event packet output from an event-based image sensor.
Figure 4:
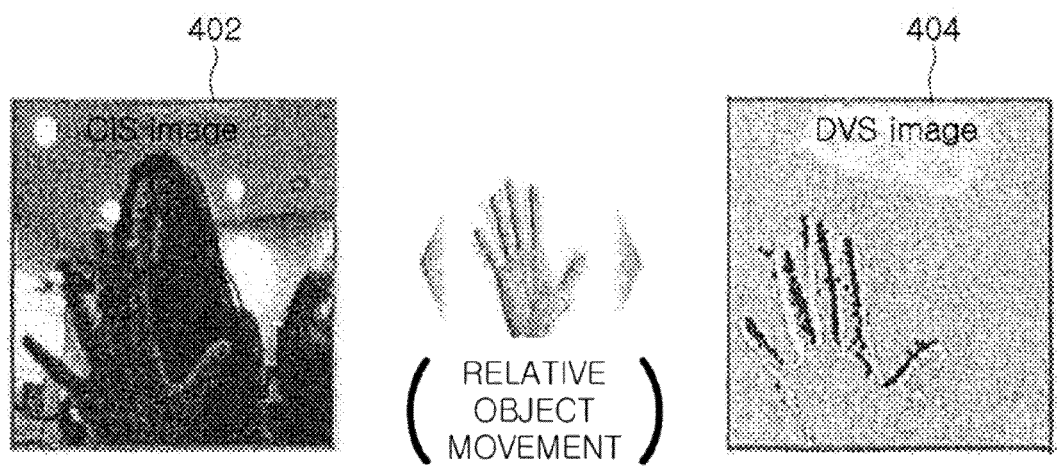
FIG. 4 depicts an example event frame in comparison to a conventional still frame.

FIG. 3A illustrates event frame creation using an event camera, in comparison to frames created with a conventional video camera that outputs image data at a constant frame rate. FIG. 3B shows an example structure of an event packet output from an event-based image sensor. FIG. 4 depicts an example event frame in comparison to a conventional still frame. Referring collectively to FIGS. 3A, 3B and 4, event cameras, as opposed to conventional video cameras, output a stream of asynchronous event data which represents the temporal contrast of light intensity onto each pixel. As shown in FIG. 3B, when the log intensity of a pixel changes by more than a threshold, an event is triggered and an event packet of an event stream is output by the image sensor organized in several fields. These fields may be a timestamp 310 representing an accurate time of the change; a pixel location 320 (x, y pixel address, i.e., column x and row y where the event occurred); and a polarity bit 330 indicating whether the change in intensity was positive or negative.

In the context of Simultaneous Localization and Mapping, each event camera (image sensor) 10-1, 10-2 responds when the camera 20 itself is moving in some surrounding. When this happens a burst of simultaneous events are triggered by the event camera. Processing system 30 uses this characteristic of the event camera to define an event frame which is a two dimensional grid (e.g. the uxv pixel grid in frame FR0 or FR1 of FIG. 2B) that accumulates the last N sensor events. As seen in FIG. 4, the resulting event frames, such as event frame 404, look like an edge map from an image sensor since only pixels close to scene edges respond to the brightness change caused by the movement. (It is noted here that to generate an initial event frame FR0, a slight movement of camera 20 may be assumed to occur at time $t_0$.) On the other hand, a conventional image frame 402, is a complete still frame generated from image information from all pixels of a pixel grid at a given time.

The use of event cameras 10-1, 10-2 for SLAM affords several advantages. First, frame times are asynchronous. As illustrated in the sequence 301 of FIG. 3A, accumulating exactly N events to construct each event frame 404 has the benefit of receiving a frame for processing only when sufficient movement of the sensor occurs. When moving fast more frames are produced since more events are triggered, and this is precisely when it is desirable for the SLAM system to respond, enabling a rapid update in pose and mapping. When there is no movement no frame may be created and no computation may be performed, thereby conserving power and resources. In a conventional camera frames are created at a fixed frame rate (sequence 305), in which a complete set of pixel data is constantly provided for every frame, regardless of whether the data has changed frame to frame.

Event cameras also exhibit the advantage of low latency. When the sensor moves the events triggered are simultaneous and therefore a frame may constitute events captured within a fraction of a millisecond. The event frames are usually a sparsely populated type of edge map, and only areas which are informative for motion processing respond to movement while other areas may be discarded without any computation needed to perform on them.

Further, the ability to control latency vs. accuracy by controlling the number of events N per event frame, provides great flexibility in design. A smaller N means that frames are created faster (see sequence 303 vs. sequence 301). When N is smaller, frames are created with lower latency and the edges will be sharper and less blurry. However, for smaller N, frames will be noisier and less informative, causing a less accurate motion estimation. A larger N gives more information for constraining the motion calculation but may result in motion blur.

Thus, event cameras are beneficial for SLAM due to their quick response to sudden movements of the camera, high power efficiency and high dynamic range, all enabling the use of SLAM in scenarios where conventional cameras might fail. The additional use of a second event camera 10-2 further increases the robustness and reliability of the SLAM system.

Figure 5A:
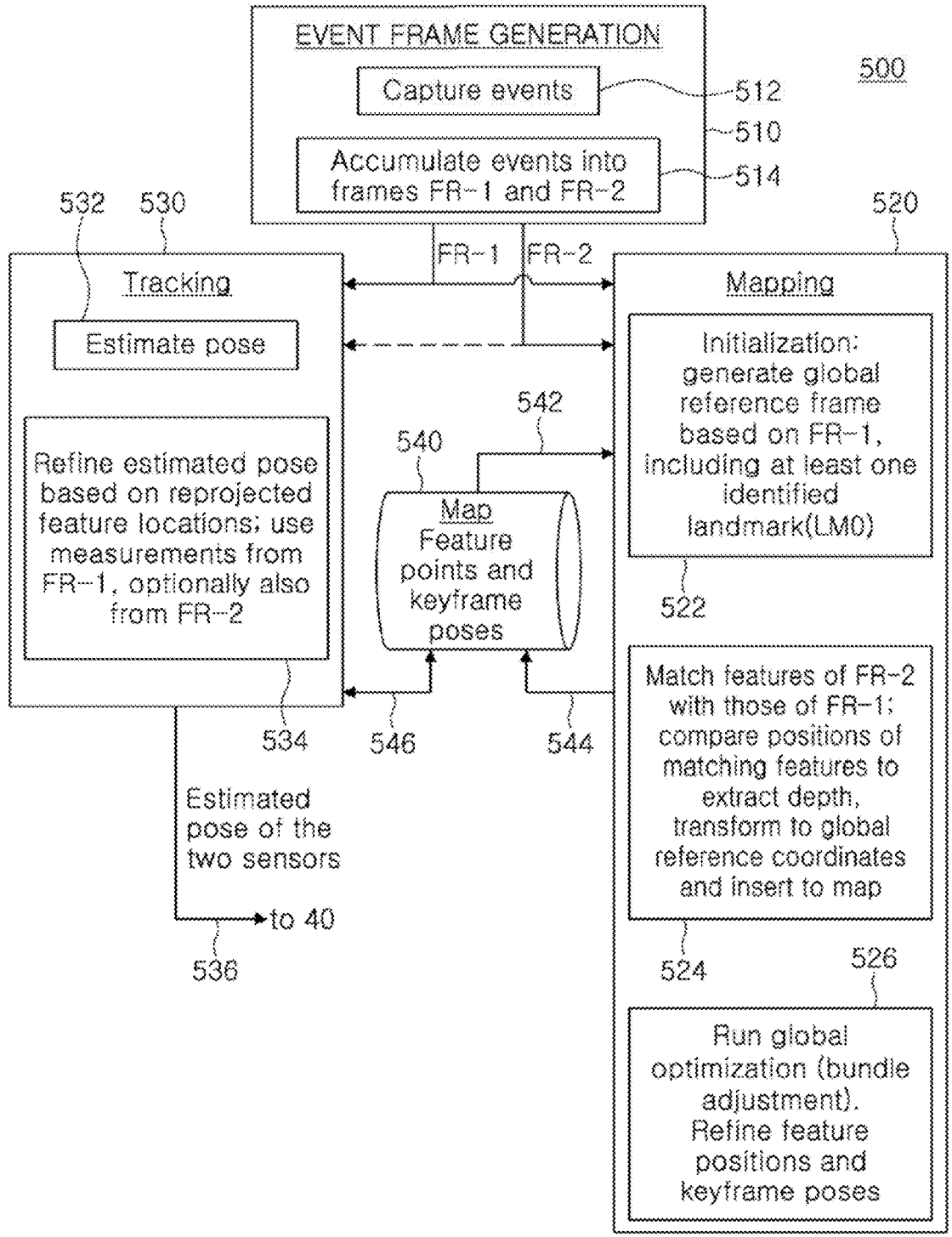
FIG. 5A is a flow chart of an example method for SLAM in accordance with the inventive concept.

FIG. 5A is a flow chart of an example method, 500, for Simultaneous Localization and Mapping in accordance with the inventive concept. The method is performed by device 50 and may be structured with an event frame generation process 510, a tracking thread 530 and a mapping thread 520. The overall approach may be a PTAM-based process that maintains these separate processing threads for tracking and mapping, with some information shared between threads. Note that alternative implementations may take a non-PTAM approach in which a single processing thread performs both the localization and the mapping.

For event frame generation, events are captured 512 by first and second image sensors 10-1, 10-2 and the captured events are accumulated 514 into first and second event frames FR-1 and FR-2, respectively. Image processing system 30 may predefine how asynchronous frames are to be generated, by defining a new event frame as being composed of image data of the latest N events. The value of N may be preset depending on the type of sensor, the number of image sensing elements of the image sensor (interchangeably referred to as pixels or "event pixels"), desired latency and accuracy, the type of environment being traversed and mapped, etc. In an extreme case, N equals 1, such that a single event may trigger a new event frame. In other cases, N may be set to several, tens, hundreds or thousands of events. Each event may be defined as an intensity change above a threshold for a single pixel, or for a predefined batch of spatially proximate pixels. With the value of N having been predefined, there may be M>N events detected to have occurred simultaneously, and in this case the new event frame may contain M events rather than just N events. The event frames FR-1 are provided to both the mapping and tracking threads 520, 530 while the event frames FR-2 are provided to at least the mapping thread 520 and optionally to the tracking thread 530 (as indicated by the dotted path).

Initially, device 50 may have no a priori knowledge of any objects or boundaries of environment E. To establish an initial registration to a reference point, an initialization process 522 may be performed as part of mapping thread 520 using initial event frames FR-1, FR-2, at a time $t_0$ when device 50 is first placed or activated within environment E. Since the first and second image sensors are event cameras, when camera 20 makes an initial movement, this triggers the detection of a multitude of simultaneous events at time $t_0$. Thus, based on the initial events, in operation 522 the method may generate a global reference frame corresponding to event frame FR-1. The global reference frame may be referred to as a first keyframe (akin to the frame FR0 exemplified in FIG. 2B) of a set of keyframes used for registration of feature locations. The global reference frame may represent M>N events that occurred at time $t_0$, or the N latest events of which the earliest detection began at time $t_0$.

In the global reference frame, a feature such as a corner or an edge of an object may be identified by a group of spatially proximate events. A feature may be identified by a set of image points, i.e., for "event pixels" (event frame pixels that are each associated with an event) that form a predetermined shape within the frame. At least one feature may be designated a reference landmark, and a point of the reference landmark may be designated as a reference landmark point $LM_0$. The reference landmark point $LM_0$ may be designated as the origin of a global coordinate system as discussed above. The feature identification may be performed by a pattern detection algorithm, of which one example is a Harris corner detector, known in the art to find feature locations. As a descriptor, a small window may be extracted from the frame around the feature location. Thus, the events of frame FR-1, i.e., the events from just the one image sensor 10-1, may be used to generate the first keyframe (where depths may be subsequently assigned to the keyframe points using events of frame FR-2).

In operation 524, the same sort of feature detection may be carried out for frame FR-2. Features of frame FR-2 are then matched with those of frame FR-1 and positions of matching features are compared to extract depth. In other words, for each event from the one image sensor 10-1, a simultaneous matching event from the other image sensor 10-2 may be used to compute the depth of the image point(s) using epipolar based depth measurement. The feature matching between the two frames may be done with a standard method, of which some examples include SIFT (scale-invariant feature transform) or SURF (speeded-up-robust-features) point/key and matching. With the depths of feature points thus determined, feature point positions may be transformed from the camera coordinate system to the global coordinate system with origin at $LM_0$, and the map points are inserted 544 to a map 540.

Meanwhile, in tracking thread 530, pose is initially estimated 532 based on frame FR-1, and the estimated pose is refined 534 based on feature locations using measurements from frame FR-1 and optionally from frame FR-2 also. More specifically, during the initialization process, an initial pose "pose-init" of image sensor 10-1 may be computed (see again FIG. 2B) with respect to the global coordinate system with origin at landmark point $LM_0$. The initial pose may be calculated based on the u, v coordinates of landmark point $LM_0$ in the first keyframe (FR0) and a depth measurement to $LM_0$. (The depth measurement may be made in operation 524 of mapping thread 520 and provided to the tracking thread 530, e.g. through paths 544, 546.) The location component of the pose may be defined with coordinates in the global coordinate system ("global coordinates"). The orientation component of the pose may likewise be set relative to the axes of the global coordinate system. (Note that the orientation aspect of the pose, as well as the axes of the global coordinate system itself, may be partly defined relative to a horizontal surface HS detected in environment E (see FIG. 1)). Since image sensors 10-1 and 10-2 are calibrated to each other, an initial pose of image sensor 10-2 may be derived from the initial pose of image sensor 10-1. The initial pose of the first keyframe may be used as a reference pose to which subsequently computed poses are defined using rotation R and translation T relative to the reference pose.

The estimated pose refining of operation 534 is performed for subsequent event frames FR-1. As described above for FIG. 2B, for any current frame following the global reference frame, the estimated pose refinement may involve making an initial guess for a new pose estimate (e.g., "pose-1-est"). Feature points of the previous frame are then re-projected to points corresponding to the pose guess for the current frame. At the pose guess, estimated coordinates such as LM0-est are thereby established for the current frame. Distances between these estimated coordinates and corresponding measured coordinates are then determined and inserted into a processor-run optimization routine that runs an iterative optimization equation to refine the estimated pose. When the optimization routine converges below a threshold, an optimized pose estimate is thereby obtained for the pose of the current frame. Optionally, the routine may also use measured feature points from frame FR-2 to further optimize the pose. The optimized pose may be output 536 to carrier device 40 as needed. The optimized pose may also be stored in map 540 via path 546 and provided to the mapping thread 520 via path 542.

For the current frame (subsequent to the global reference frame), mapping thread 520 may run 526 a global optimization using the optimized pose for that frame. The global optimization may be a bundle adjustment in which feature positions and keyframe poses are refined. The refined feature positions and keyframe poses may then be stored 544 within the map 540 to update the same.

Figure 5B:
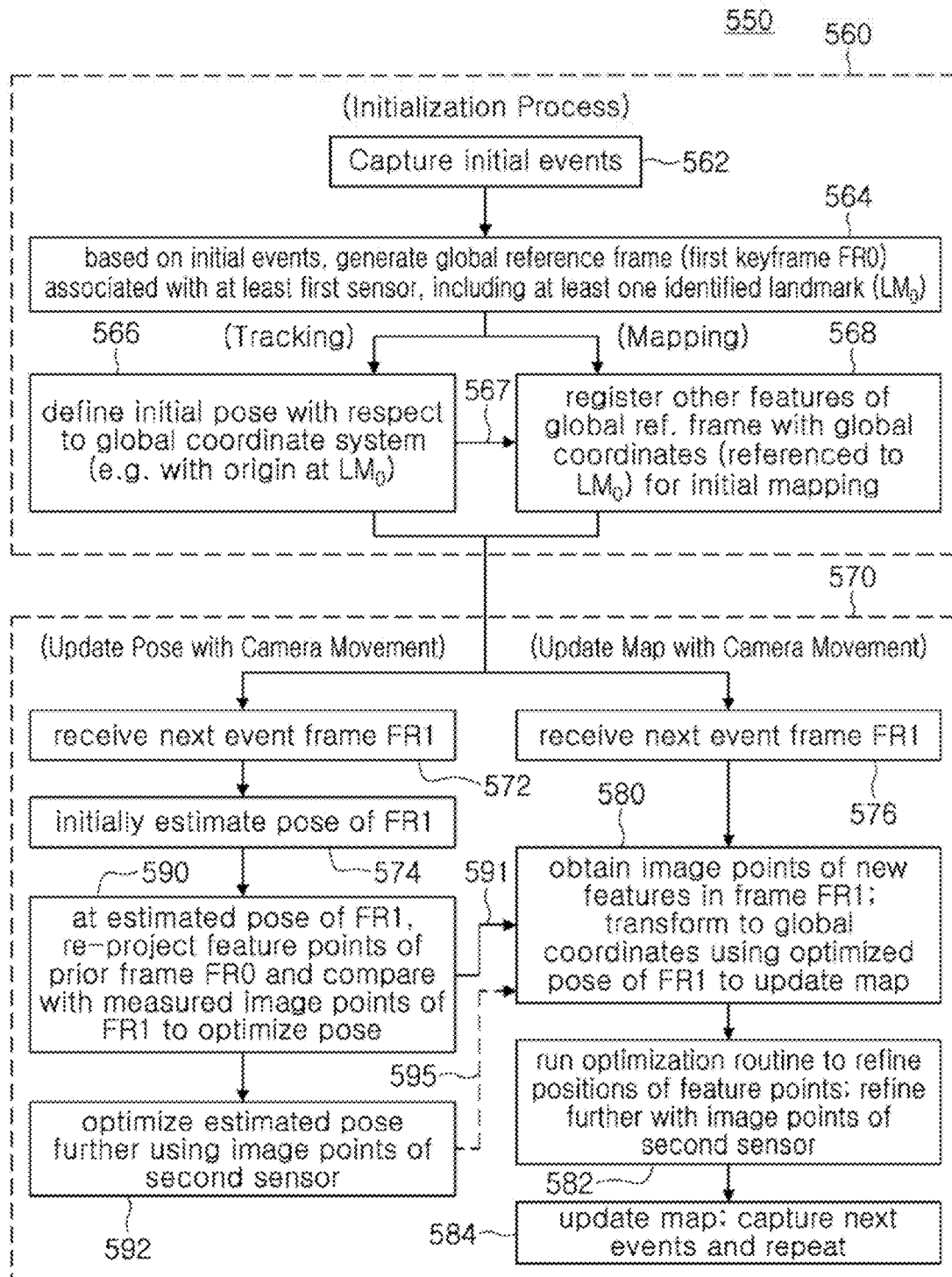
FIG. 5B is a flow chart of an example sub-process that may be used as part of the method of FIG. 5A.

FIG. 5B is a flow chart illustrating a sub-process 550 that may be used within the method 500 of FIG. 5A. Sub-process 550 is structured with an initialization process 560 followed by an operation set 570 for pose/map updating with camera movement. During initialization 560, initial events are captured 562 and a global reference frame (referred to here interchangeably as first keyframe FR0) is generated 564 based on the initial events. The global reference frame may be associated with at least the first sensor 10-1 and includes at least one identified landmark $LM_0$. In the tracking thread, an initial pose "pose-init' may be defined 566 with respect to the global coordinate system designated with landmark point $LM_0$ at its origin. In the mapping thread, other object features identified in first keyframe FR0 may be identified and registered 568 with global coordinates to provide an initial mapping of the environment. Here, locations of image points with respect to camera 20 may be first defined by coordinates in the camera coordinate system, and these coordinates may be transformed, with knowledge of the pose (obtained 567), to global coordinates.

A next event frame FR1 is generated based on the next N events detected immediately after those of the first keyframe FR0, by at least the first sensor 10-1. The next event frame FR1 is received 572 by the tracking thread and also by the mapping thread (576). The tracking thread initially estimates 574 the pose of frame FR1 using a pose guess as described above. Features of frame FR1 may be identified in the same or similar way as was done for the keyframe FR0, e.g. using a Harris corner detector or other suitable technique. Note that such feature detection need not wait until N events for an entire event frame are accumulated, but may instead proceed as individual events or a smaller batch of K events (K<N) are received. At the initially estimated pose of frame FR1, feature points of the prior frame FR0 are re-projected 590 and compared with measured image points of frame FR1 to optimize the pose estimate. In this process, features of frame FR1 may first be matched with those of keyframe FR0 in a similar matching method as in the initialization process, e.g., using SIFT or SURF. An optimization routine such as a gradient descent based routine is run to optimize the pose. This routine may determine optimum values of rotation R and translation T (relative to the reference pose "pose-init") that minimizes distances between corresponding estimated points and measured points (as illustrated above in FIGS. 2C-2E). The optimized pose is provided 591 to the mapping thread. Optionally, the pose is optimized further 592 using measured image points of the second sensor 10-2 (from frame FR-2 of FIG. 5A) and this optimized pose is instead provided 595 to the mapping thread.

In operation 580 of the mapping thread new features of frame FR1, i.e., not matched with any feature in keyframe FR0, are identified. The locations of their image points, obtained in camera coordinates, are transformed to global coordinates using the optimized pose. These new features may be stored to update the map.

In operation 582, optimization of the positions of all features may be performed by running an optimization routine based on bundle adjustment, which refines their positions and also refines the pose. The optimization may also optimally align a point cloud representing the 3D image points of the current frame with a point cloud of a previous frame or previous keyframe. The refined feature positions and pose may be stored 584 in the map to update the same, whereupon the set of operations 570 may be repeated for the next set of captured events. That is, features of each newly obtained event frame may be matched with those of the previous event frame to derive positional information. Moreover, the positions may be further refined with image points of the second sensor 10-2. That is, measurements from the second sensor 10-2 may be added to an error function of the optimization routine. These measurements were already made for the purpose of feature point initialization and therefore come at no additional computational cost.

The optimization routine of operation 582 (or 526) may be based on a batch technique of bundle adjustment. Specifically, due to the imperfect detection of light by the sensors 10-1, 10-2, some of the detected events may actually be errors or noise. That is, any given event or group of proximate events comprising a feature may not actually represent a precise location of the feature in the environment, or may represent a distorted or noisy version of the feature. To reduce errors of this nature, the optimization routine may use a bundle adjustment process to average/filter image data and thereby refine the positions of the features in frame FR1 and also refine the previously optimized pose. The bundle adjustment process may minimize an error function consisting of the difference between measured positions of features and the estimated position of those features by projecting from the estimated pose and the estimated 3D position (i.e., the above-discussed reprojection error). In an example, the optimization routine may utilize a gradient descent based error function. In another example, the optimization routine may involve an iteration process that minimizes the following objective function:

$$\{\{u_2 \cdots u_N\}, \{p'_1 \cdots p'_M\}\} = \underset{\{\{u\},\{p\}\}}{\operatorname{argmin}} \sum_{i=1}^{N} \sum_{j \in S_i} Obj(|e_{ji}|/\sigma_{ji}, \sigma_T). \quad \text{eqn. (1)}$$

The objective function of eqn. (1) is described in *Klein & Murray, Parallel Tracking and Mapping for Small AR Workspaces* (*ISMAR* 2007). In eqn. (1), Si is a set of image measurements associated with the ith keyframe; Obj (•, $\sigma_T$) is the Tukey biweight objective function; $\sigma_T$ is an estimate of the distribution's standard deviation; j is the jth map point; $e_{ji}$ is a reprojection error vector for the jth map point and the ith keyframe; and $u_2 \ldots u_N$ and $p'_1 \ldots p'_M$ represent points on the map.

It is noted here that some embodiments may be configured for a sparse depth calculation. Depth may be calculated sparsely by only calculating depth information for regions that are found to be informative by an interest point detector in one of the sensors 10-1, 10-2. This saves computational power since calculating a dense depth map is a computationally intensive task.

As noted above, any event frame may be designated as a keyframe based on at least one predefined criterion, such as whether at least at least a threshold number of new features are present. Further, as mentioned earlier, the first and second sensors 10-1, 10-2 are calibrated (their relative pose is known) and only the poses of the first sensor 10-1 may be represented as parameters for the optimization. Therefore, reprojection of a feature captured by the second sensor 10-2 may be performed by taking the pose parameter of the first sensor 10-1, transforming it to the pose of the second sensor 10-2 using the known calibration, and then projecting the 3D feature onto the second sensor. In some embodiments, this may also be done in the optimization process of the tracking thread (the pose estimation) but at the expense of additional measurements that would be performed every frame in the two sensors 10-1, 10-2.

In the above-described methods, the use of a stereo configuration with dual event cameras may provide certain advantages. For new feature discovery (new feature initialization), the use of two event cameras may afford a more accurate disparity calculation as compared to a stereo configuration with constant frame rate cameras employed in conventional SLAM systems. Here, disparity refers to the difference in position of image features in the two sensors created by the different viewpoints. That is, the use of two event cameras as described above may beneficially reduce the chance of a false disparity. For each feature found in one frame (of one sensor) a corresponding feature should be found in the other frame (of the other sensor). Since both frames are typically created in a very short time interval with the event cameras 10-1, 10-2 as compared to constant frame rate cameras, this reduces the chance of a false match being found. In addition, as mentioned earlier, a sparse depth calculation is afforded with the use of the dual event cameras.

Figure 6:
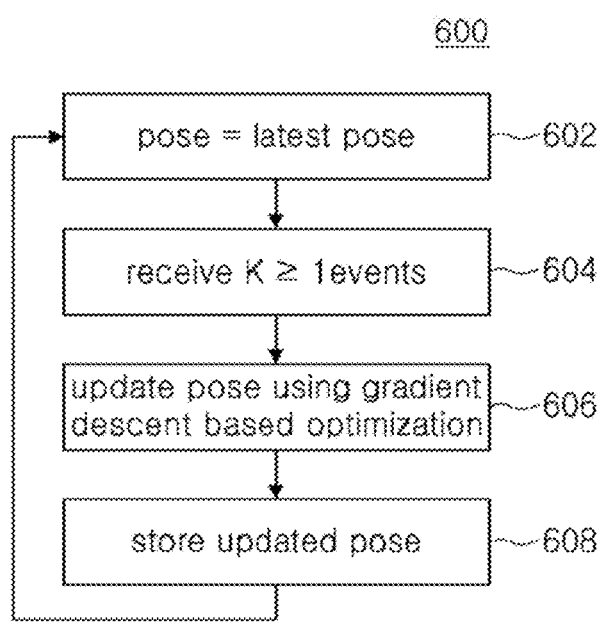
FIG. 6 is a flow chart of an example pose optimization method in accordance with the inventive concept.

FIG. 6 is a flow chart of an example method 600 of pose optimization in accordance with the inventive concept.

Method 600 may be used as part of a SLAM system and may be an alternative to the pose optimization operations within the method 500 of FIG. 5A (e.g. operation 534). Initially, at block 602 stored pose parameters equal the latest computed pose, which may be the initial pose pose-init or a subsequently determined pose after camera 20 has moved. A next batch of K≥1 events is then received 604, where K is an integer value that may be preset. (The K events may be events counted from one of the first and second image sensors 10-1, 10-2, or, only matching events from both image sensors 10-1, 10-2 may be counted to arrive at the K events.) The pose is then updated 606 using at least using at least one optimization step of a gradient descent based optimization. The updated pose is stored/output 608 and thereafter the method 600 operations repeat. In one example, K is preset to a value of at least one order of magnitude smaller than the number of pixels in the first or second image sensor (less than 10% of the number of pixels). In another example, K is preset to less than 2% of the number of pixels; and in a further example, K is preset to less than 1% of the number of pixels. In an extreme case, K is preset to one, whereby the pose is updated for every event in operation 606.

Gradient descent is an optimization technique used to find a local minimum of a function. In general, this is done by determining the gradient of the function at a current point, and by taking steps proportional to the negative of this gradient at the current point. In the current discussed method 600, the gradient descent optimization 606 may minimize the following error function:

$$E(R, t) = \sum_{i,j} \varphi(Rx_{ij} + t)^2 \quad \text{(eqn. 2)}$$

where R is rotation, t is translation, $x_{i,j}$ represents a 3D point in the camera coordinate system at coordinates (i, j) which iterate over all pixels in the 3D projected image of any frame, E (R, t) denotes an error between predicted and measured pose parameters R, t associated with the 3D image, and φ denotes a signed distance function. A signed distance function may be considered a voxel-based data structure in which a 3D environment is discretized into voxels, and each voxel is assigned a value representing an approximate distance to a nearest surface of an object in the environment. The assigned voxel value may be zero for voxels coinciding with a boundary of the object, a negative value proportional to a distance away from the object surface, and a positive value proportional to a distance from the object surface inside the object. Eqn. (2) may be referred to as a cost function, in which optimized values of R and t are iteratively sought to minimize the value of the error E(R, t) over the range of i, j.

The gradient descent based optimization of method 600 exhibits certain advantages over conventional approaches to solving the pose optimization problem, such as the Gauss Newton iterative approach taken in Bylow, Strurm et al., *Real-Time Camera Tracking and 3D Reconstruction Using Signed Distance Functions, Robotics: Science and Systems*, 2 (2013)) (note that eqn. (2) above is also found in the Bylow article). For instance, if a Gauss Newton iterative approach at each event or batch of events were to be attempted for pose optimization in the case of a dual event-based camera, the processing would be too computationally heavy and therefore impractical in many applications. On the other hand, the approach of method 600 takes advantage of the continuous and random nature of the input stream of events, and keeps the camera pose cost function to a minimum by performing the gradient descent step 606 for each event or batch of events (K>1 events in the latter case).

One type of gradient descent algorithm that may be utilized is the Nesterov Accelerated Gradient Descent method. This method is often used in Machine Learning to minimize an objective function stochastically, using a random example(s) from a training set. Such a random example(s) may be referred to as a "training example" or a "batch of examples". In operation 606 of method 600, the training example or batch of examples may be replaced by an event or batch of events to achieve the cost function minimization (and thereby the pose optimization).

Figure 7:
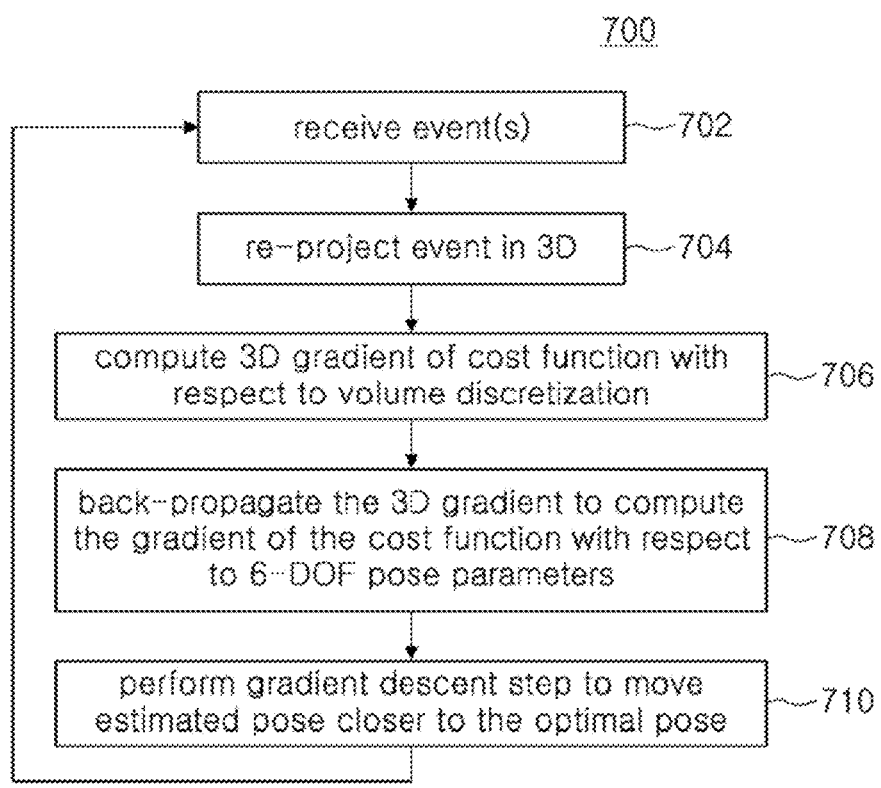
FIG. 7 is a flow chart of an example pose optimization method employing gradient descent based optimization, in accordance with the inventive concept.

FIG. 7 is a flow chart of an example optimization method 700 employing gradient descent optimization in accordance with the inventive concept. As in the method 600 of FIG. 6, method 700 may be used as an alternative to the pose optimization described for the method of FIG. 5A. The method 700 operations may likewise be performed for each $K \geq 1$ events, where K is a preset integer as discussed above for the method 600. When K events are received 702, the events are each re-projected 704 in three dimensions. The 3D gradient of the cost function is then computed 706 with respect to "volume discretization". Volume discretization assumes a map is represented as a volume. Typically, there are two ways for such volume representation: i) a Truncated Signed Distance Function (TSDF); and ii) a Map Point Likelihood Function (MPLF). A TDSF function stores in each voxel the distance to the surface of an object as mentioned above for signed distance functions, but assigns a maximum value (such as 1.0) to voxels located beyond a threshold distance from the surface. A TDSF volume representation is commonly used to fuse depth information. In a MPLF representation, each voxel contains a probability of the existence of a map point at the voxel location.

In the next operation 708, the gradient is "back-propagated" (e.g., using the "chain rule") to compute the gradient of the cost function with respect to the 6-DOF pose parameters. (The chain rule is a mathematical formula used in calculus for calculating the derivative of the composition of two or more functions.) Lastly, a gradient descent iteration is performed 710 to move the estimated pose closer to the optimal pose. The preceding operations are then repeated each time K events are received. In one example, the estimated pose may be initially set equal to the previously computed pose, which leverages the fast, asynchronous acquisition of events.

With the above approach in which pose is updated for every K events, contrary to constant frame rate cameras, there is no need to wait until an entire conventional frame period (typically ~33 ms for 30 f/s) to process events and update the pose. As a result, a higher pose update rate is achievable with the dual event camera/gradient descent based approach of the present inventive concept. The inventive concept also allows for a reduction in jitter, a well-recognized problem in conventional virtual reality SLAM systems. For instance, with a conventional system (e.g., in Bylow, supra) the error accumulated over 33 ms can be high, so the correction that occurs each frame can be large, and generate jitter and discomfort to the user, particularly in a virtual reality system. The inventive concept reduces such jitter since the pose is corrected very frequently (every K events), whereby the pose update is always small and the trajectory is smooth.

Figure 8:
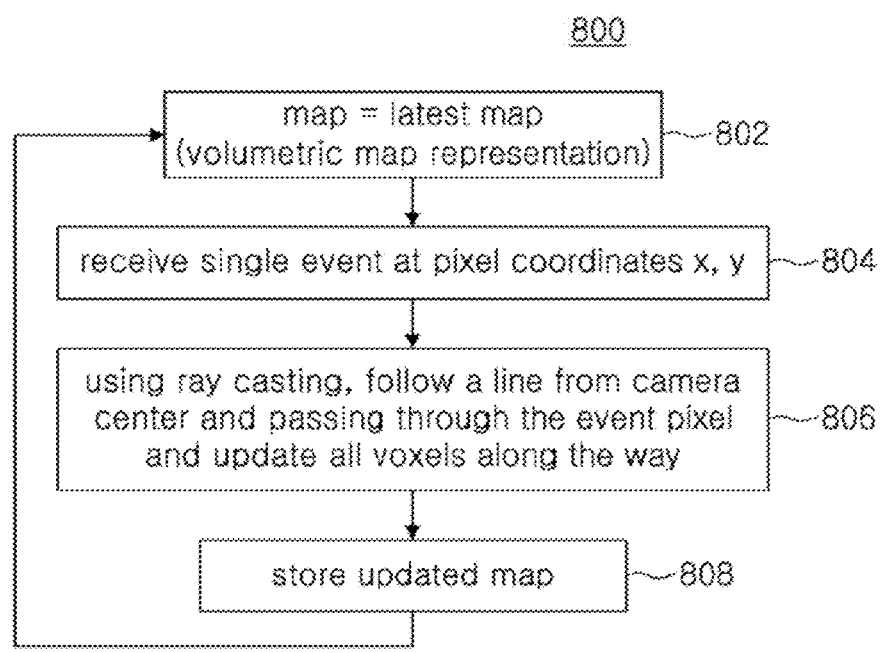
FIG. 8 is a flow chart of a map updating method in accordance with the inventive concept.

FIG. 8 is a flow chart of a map updating method, 800, in accordance with the inventive concept. Method 800 may be used as an alternative to the map optimization described above for the method of FIG. 5A. Instead of performing optimization through analysis of numerous newly obtained image points, a ray casting based update is made for each newly detected event. Method 800 may be used in conjunction with the pose updating methods 600 or 700 just discussed.

At an initial block 802, stored map data may represent the latest map of the environment E, which may be the initial map or a map that was further built up after camera 20 moved. Surfaces of objects may be reflected in the map by a volumetric representation such as either the TDSF or MPLF representation discussed earlier. A single event of one image sensor 10-1 is then received (804), where the event corresponds to pixel coordinates x, y of a projected image plane. Here, it may be assumed that the image sensor coordinates x, y associated with the event ("the event pixel") may be correlated with pixel coordinates x, y of a virtual 2D image plane ("the virtual event pixel") projected from the viewpoint of the camera, that is, the camera center. In ray casting, such a virtual 2D image plane is projected at a location between the camera viewpoint and a virtual 3D environment comprising a set of voxels modeling the environment. Here, it may be assumed that the camera viewpoint is a viewpoint corresponding to the updated pose computed in method 600 or 700. Also, the single event considered here may be the first of the K events that were used to generate the updated pose.

In a ray casting operation (806), a virtual line is drawn from the viewpoint and passes through the projected image plane at the virtual event pixel. The line continues into the set of voxels and intersects at least one of the voxels along the way. The intersected voxel(s) is then updated by assuming that an edge of an object exists in that voxel at a location at which the ray enters the voxel. The volumetric map representation (whether it is a TSDF or MPLF representation) is thereby updated and stored (808).

In accordance with various embodiments described above, a SLAM system employing a dual event camera is able to update a camera pose for each event or relatively small batch of K events. Thus, a SLAM system according to various embodiments of the inventive concept may outperform conventional SLAM systems in power efficiency, latency and robustness to high speed motion.

In particular, power efficiency may be improved by processing only a sparse stream composed of events. In contrast, a SLAM system deploying a conventional constant frame rate camera processes data representing each pixel for every frame. Further, latency may be faster than in a SLAM system with a constant frame rate camera. For instance, an embodiment may use a state of the art event camera that typically sends >1 million events/second. In this case, sub-millisecond latency may be reached. Moreover, a SLAM system according to the inventive concept may exhibit robustness to ultra-high speed motion due to such low latency.

The processing of the methods described above may each be performed by at least one processor of image processing system 30. The at least one processor may be dedicated hardware circuitry, or, at least one general purpose processor that is converted to a special purpose processor by executing program instructions loaded from memory.

Figure 9:
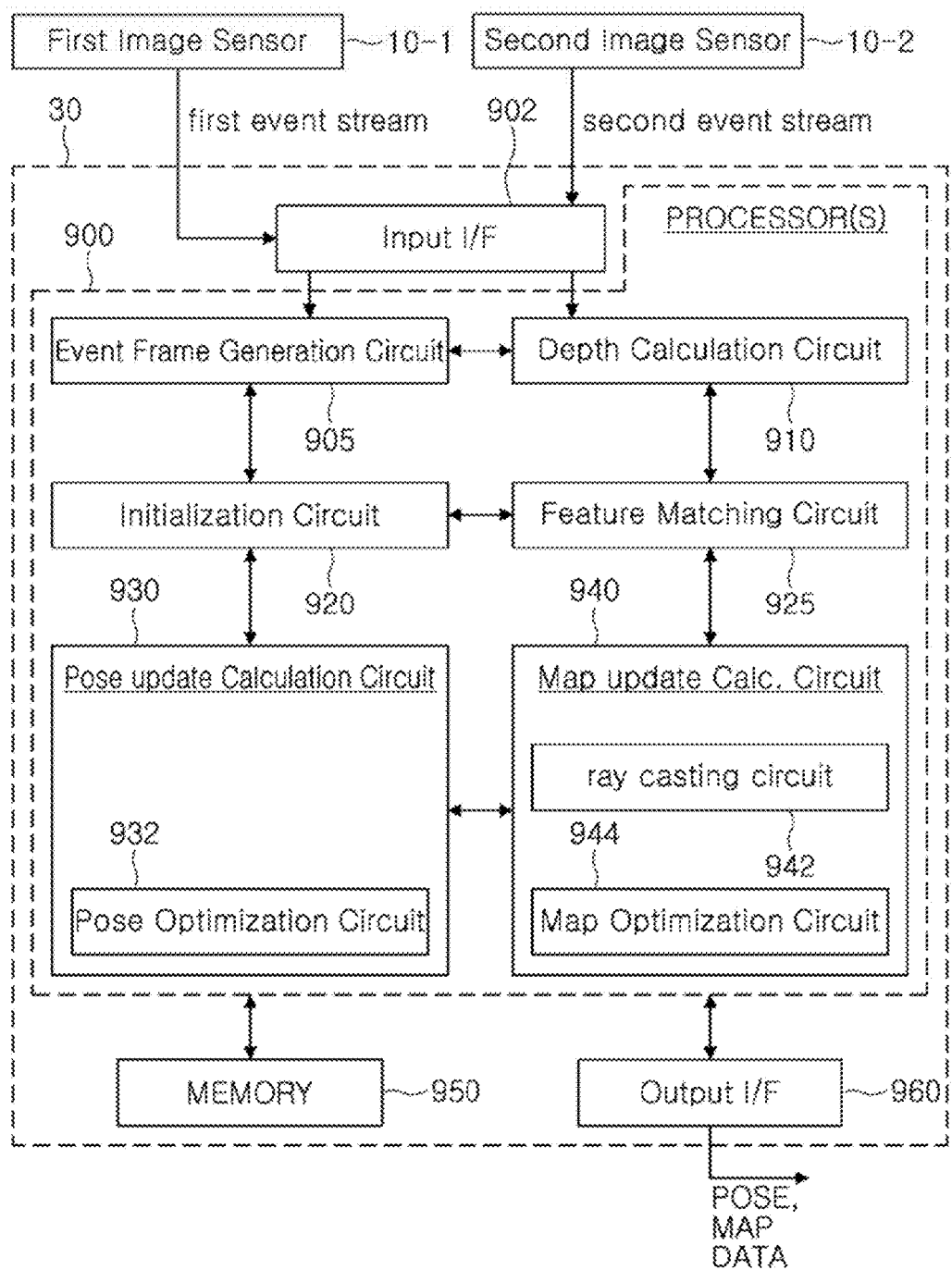
FIG. 9 is a functional block diagram of an example dual event-based camera according to the inventive concept.

FIG. 9 is a functional block diagram of an example configuration for camera 20 according to the inventive concept. Camera 20 includes first and second image sensors 10-1 and 10-2, and image processing system 30, shown in an exemplary configuration. Image processing system 30 includes: at least one processor 900 which performs the processing in the above-described methods; a memory 950; an input interface circuit 902 and an output interface circuit 960.

Processor 900 may be part of an integrated circuit and may include various circuits, each for performing a particular function within one or more of the methods described above. To this end, processor 900 may include an event frame generation circuit 905, a depth calculation circuit 910, an initialization circuit 920, a feature matching circuit 925, a pose update calculation circuit 930 and a map update calculation circuit 940. Each of the various circuits 905, 920, etc. of processor 900 may be formed by common or different circuitry within processor 900 executing program instructions read from memory 950.

First and second image sensors 10-1 and 10-2 may output first and second event streams, respectively, to input interface circuit 902, which provides the data thereof in suitable form to processor 900. Event frame generation circuit 905 may generate event frames for every N or M events of each image sensor as described above, while depth calculation circuit 910 may compute depth for each commonly imaged point (or each point of matching features) by the two image sensors 10-1, 10-2. Initialization circuit 920 may perform the processing for the above-described initialization process 510. Feature matching circuit 925 may carry out the various feature identification, searching and matching such as those within initialization process 560 and operation 522 of method 500. Processing for separate pose updating and mapping, for a PTAM implementation, may be handled by pose update calculation circuit 930 and map update calculation circuit 940, respectively. Pose update calculation circuit 930 may include a pose optimization circuit 932 to perform the pose optimization of FIGS. 5A, 5B or the gradient descent based optimization of FIG. 6 or 7. Map update calculation circuit 940 may include a ray casting circuit 942 for the ray casting of FIG. 8, and a map optimization circuit 944 to perform the map optimization described for FIGS. 5A, 5B.

Memory 950 may be used by one or more of the shown circuits 905, 910, etc. of processor 900 for interim storage during calculations, and for storing computed pose and map data. Memory 950 may also store program instructions read by and executed by processor 900 to carry out its operations. Output interface 960 may output pose and map data generated by processor 900 as required by the particular application running within device 50 of FIG. 1.

It is noted here that since camera 20 is configured to implement SLAM, camera 20 may interchangeably be referred to as a SLAM system. Further, camera 20 may be included as part of electronic device 50 having other functionality (as mentioned earlier in connection with FIG. 1). Some examples of the electronic device include but are not limited to a robot, a smart phone, a drone, an autonomous vehicle, a medical imaging apparatus, a portable electronic device, a personal computer, a notebook computer, a tablet, and a wearable device. A portable electronic device may be sized and configured to be easily carried in a typical user's single hand.

Exemplary embodiments of the inventive concept have been described herein with reference to signal arrows, block diagrams and algorithmic expressions. Each block of the block diagrams, and combinations of blocks in the block diagrams, and operations according to the algorithmic expressions can be implemented by hardware accompanied by computer program instructions. Such computer program instructions may be stored in a non-transitory computer readable medium that can direct a computer, other programmable data processing apparatus, or other devices to function in a particular manner, such that the instructions stored in the computer readable medium produce an article of manufacture including instructions which implement the function/act specified in the flowchart and/or block/schematic diagram.

The term "processor" as used herein is intended to include any processing device, such as, for example, one that includes a central processing unit (CPU) and/or other processing circuitry (e.g., digital signal processor (DSP), microprocessor, etc.). Moreover, a "processor" includes computational hardware and may refer to a multi-core processor that contains multiple processing cores in a computing device. Various elements associated with a processing device may be shared by other processing devices.

The above-described methods according to the present technology can be implemented in hardware, firmware or via the use of software or computer code that can be stored in a recording medium such as a CD ROM, RAM, a floppy disk, a hard disk, or a magneto-optical disk or computer code downloaded over a network originally stored on a remote recording medium or a non-transitory machine readable medium and to be stored on a local recording medium, so that the methods described herein can be rendered using such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing described herein.

While the inventive concept described herein has been particularly shown and described with reference to example embodiments thereof, it will be understood by those of ordinary skill in the art that various changes in form and details may be made therein without departing from the spirit and scope of the claimed subject matter as defined by the following claims and their equivalents.

What is claimed is:

1. A method for simultaneous localization and mapping (SLAM), comprising:

receiving, from first and second image sensors, first and second event streams, respectively, each comprising a plurality of event packets indicating events corresponding to points of surfaces in an environment, wherein a number of events is controlled in event frame units and each event frame is formed by movement of the first and second image sensors;

computing depths of the points represented by the first event stream based on relative pixel locations of common points represented by the second event stream; and updating a map of the environment, based at least on the points represented by the first event stream and the computed depths thereof, wherein the events are triggered when a log intensity of a pixel changes by more than a threshold, wherein each of the event packets of the events comprises a time stamp representing a time of the pixel intensity change, a pixel address within a pixel grid of the first or second image sensor, and a polarity bit indicating whether the pixel intensity change was positive or negative.

2. The method of claim 1, further comprising running an optimization routine to optimize map locations.

3. The method of claim 2, wherein the optimization routine minimizes an error function using a first set of points represented by events of the first image sensor and a second set of points represented by events of the second image sensor.

4. The method of claim 1, further comprising:
dynamically computing a pose of at least the first image sensor with respect to a reference element in the environment.

5. The method of claim 4, wherein dynamically computing a pose comprises initially estimating a pose with the aid of an Inertial Measurement Unit (IMU).

6. The method of claim 4, wherein dynamically computing a pose and updating a map are performed using separate processing threads of a parallel tracking and mapping (PTAM) process.

7. The method of claim 4, wherein the dynamic computing of the pose comprises optimizing the pose using a gradient descent based optimization method.

8. The method of claim 7, comprising representing the map as a volumetric map with a Truncated Signed Distance Function (TSDF) or a Map Point Likelihood Function (MPLF).

9. The method of claim 8, wherein updating a map of the environment comprises updating the volumetric map for each event received from the first image sensor using ray casting.

10. The method of claim 4, wherein the dynamically computing a pose comprises:
re-projecting a surface point corresponding to each newly received event in three dimensions (3D);
computing a 3D gradient of a cost function with respect to volume discretization;
back propagating the gradient to compute the gradient with respect to six degrees of freedom pose parameters; and
performing a gradient descent iteration to move an estimated pose closer to an optimal pose.

11. The method of claim 10, wherein the gradient is back propagated using the chain rule.

12. The method of claim 4, wherein the dynamic computing of the pose comprises determining distances between measured points and points of an initially estimated pose, the initially estimated pose being a previously computed pose corresponding to a previous event frame.

13. A simultaneous localization and mapping (SLAM) system comprising:
a first image sensor that provides a first event stream of event packets indicating events corresponding to points of surfaces in an environment;
a second image sensor arranged to have an overlapping field of view with that of the first image sensor and providing a second event stream of event packets indicating events corresponding to points of surfaces in the environment;
an image processing system comprising at least one processor that executes instructions read from a memory to:
compute depths from the first and second image sensors stereoscopically based on points of matching features represented by the first and second event streams; and
update a map of the environment, based at least on the points of matching features represented by the first event stream and the computed depths thereof,
wherein a number of events is controlled in event frame units and the event frame is formed by the movement of the first and second image sensors,
wherein the events are triggered when a log intensity of a pixel changes by more than a threshold,
wherein each of the event packets of the events comprises a time stamp representing a time of the pixel intensity change, a pixel address within a pixel grid of the first or second image sensor, and a polarity bit indicating whether the pixel intensity change was positive or negative.

14. The SLAM system of claim 13, wherein the updating of a map is performed using separate processing threads of a parallel tracking and mapping (PTAM) process running on the at least one processor,
wherein the at least one processor represents the map as a volumetric map with a Truncated Signed Distance Function (TSDF) or a Map Point Likelihood Function (MPLF).

15. The SLAM system of claim 13, wherein the at least one processor dynamically compute a pose of at least the first image sensor with respect to a reference element in the environment,
wherein the dynamic computing of the pose comprises optimizing the pose using Nesterov Accelerated Gradient Descent method as a gradient descent based optimization method.

16. A non-transitory computer-readable recording medium storing instructions that, when executed by at least one processor, implement a method for simultaneous localization and mapping (SLAM), the method comprising:
receiving, from a first image sensor and a second image sensor, a first event stream and a second event stream, respectively, of event packets indicating events corresponding to points of surfaces in an environment,
computing depths of the points represented by the first event stream based on relative locations of common points represented by the second event stream; and
dynamically computing a pose of at least the first image sensor with respect to a reference element in the environment, and updating a map of the environment, based at least on the points represented by the first event stream and the computed depths thereof,
wherein a number of events is controlled in event frame units and the event frame is formed by movement of the first and second image sensors.

17. The non-transitory computer-readable recording medium of claim 16, wherein the dynamic computing of the pose comprises updating the pose for each K events of the first event stream, where K is a predefined integer and is at least one order of magnitude less than a total number of image capture elements of the first or second event sensor.

18. The non-transitory computer-readable recording medium of claim 16, wherein dynamically computing a pose and updating a map are performed using separate processing threads of a parallel tracking and mapping (PTAM) process.

19. The non-transitory computer-readable recording medium of claim 16, wherein the dynamic computing of the pose comprises optimizing the pose using a gradient descent based optimization method.

20. The non-transitory computer-readable recording medium of claim 19, wherein the method comprises representing the map as a volumetric map with a Truncated Signed Distance Function (TSDF) or a Map Point Likelihood Function (MPLF).

* * * * *